United States Patent [19]
Butler et al.

[11] Patent Number: 5,167,145
[45] Date of Patent: Dec. 1, 1992

[54] MEASUREMENT OF BLOOD COAGULATION TIME USING INFRARED ELECTROMAGNETIC ENERGY

[76] Inventors: David M. Butler, 529 Chesapeake Ave., Stevensville, Md. 21666; Harold B. Kirkpatrick, 830 W. 40th St., Baltimore, Md. 21217; John H. Staehlin, Mays Chapel Rd., Lutherville, Md. 21093

[21] Appl. No.: 584,789

[22] Filed: Sep. 19, 1990

[51] Int. Cl.⁵ .................. B01N 21/17; B01N 33/49
[52] U.S. Cl. ................................ 73/64.43; 356/39; 436/69; 422/73
[58] Field of Search .............. 73/64.1; 250/564, 573, 250/576; 356/39; 436/69; 422/73

[56] References Cited

U.S. PATENT DOCUMENTS

| | | | |
|---|---|---|---|
| 3,458,287 | 7/1969 | Gross et al. | 436/69 |
| 3,658,480 | 4/1972 | Kane et al. | 73/64.1 X |
| 3,833,864 | 9/1974 | Kiess et al. | 73/64.1 X |
| 4,217,107 | 8/1980 | Saito et al. | 73/64.1 X |
| 4,454,752 | 6/1984 | Scordato | 73/64.1 |
| 4,492,462 | 1/1985 | Pross et al. | 73/64.1 X |
| 4,740,460 | 4/1988 | Sokata et al. | 73/64.1 X |
| 5,004,923 | 4/1991 | Hillman et al. | 250/341 |

Primary Examiner—Hezron E. Williams
Assistant Examiner—Michael J. Brock
Attorney, Agent, or Firm—Aquilino & Welsh

[57] ABSTRACT

A method and apparatus for detection of blood coagulation using infrared electromagnetic transmission changes through a sample from a source of infrared energy to suitable detection electronics producing a peak signal representative of the clotting time.

13 Claims, 6 Drawing Sheets

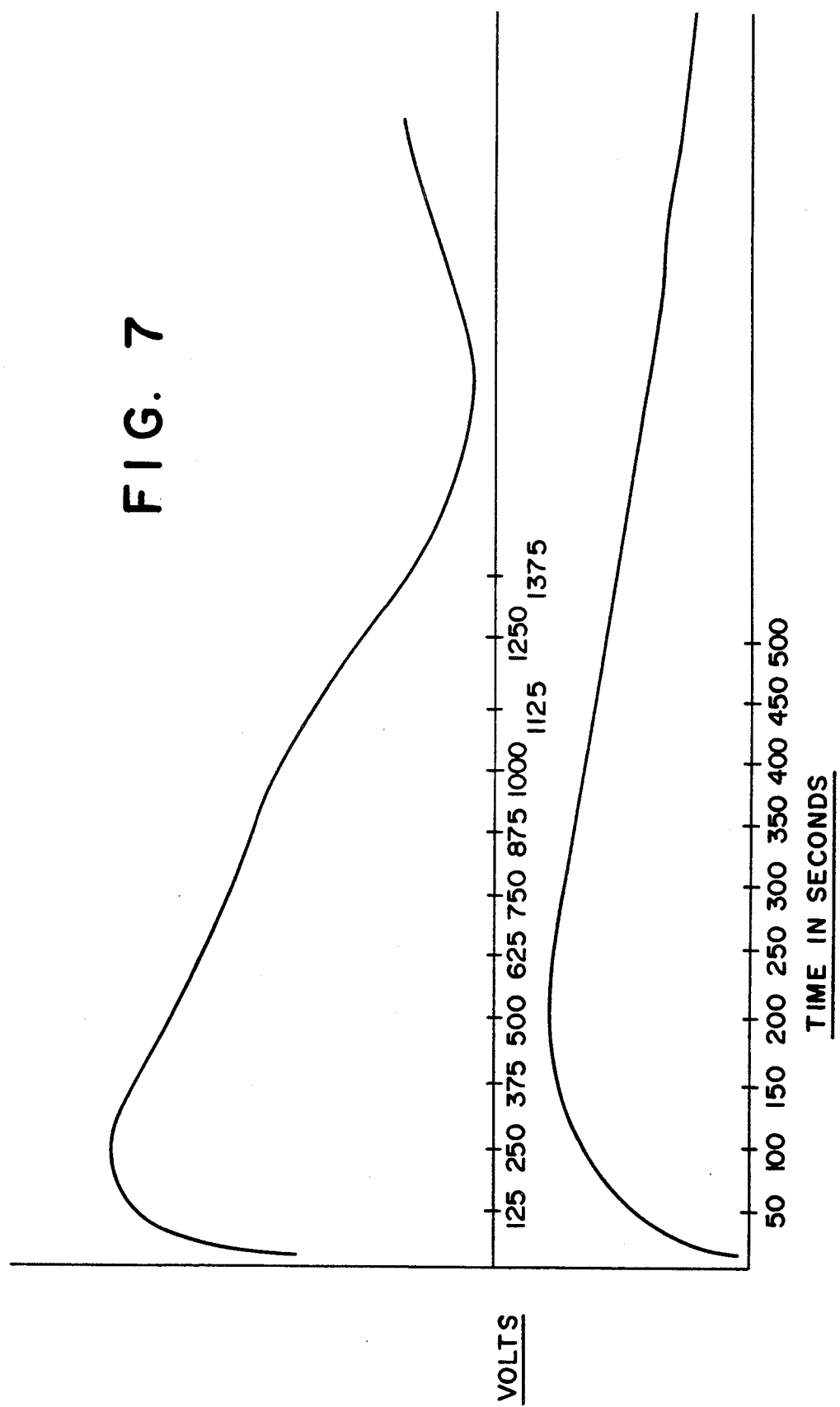

MEASUREMENT OF BLOOD COAGULATION TIME USING INFRARED ELECTROMAGNETIC ENERGY

FIELD OF THE INVENTION

The invention relates to the measurement of multiple sequential changes which occur during blood coagulation, and particularly to an apparatus and method for detecting, recording and timing this process, using electromagnetic infrared transmission through a sample to a photodetector.

BACKGROUND OF THE INVENTION

At the present time, approximately 85% of all blood coagulation testing is carried out in the laboratory by means of a widely discredited and time-consuming procedure. An urgent need therefore exists for an instrument which is capable of measuring accurately and promptly the clotting time of blood at the patient's bedside or in the surgical suite. The value of a portable device of this kind relates primarily to surgical procedures which require the administration of Heparin. Immediate, accurate and reliable measurement of clotting time are essential to determination of the correct Heparin dosage in order to prevent possibly fatal hemorrhage or thrombosis. Such a portable automatic instrument, which can be operated by a nurse, without the intervention of a doctor or laboratory technician, will therefore satisfy an important unmet need in current medical practice.

Prior art instruments for determining the process of blood coagulation almost without exception have been based on the automation of established and well known manual test methods such as Lee White, and ACT (Activated Clotting Time). As such, they share the limitations of the manual methods (the ambiguity of the end point and the related variability of test to test results). Such variability is amplified by the interaction of the coagulating blood with the solid bodies which constitute an essential element of the automatic devices based on Lee White and ACT. All prior art patents reviewed hereinbelow, which are based on Lee White and ACT and various modifications thereof, employ intrusive solid elements which introduce, through their interaction with the blood, an undetermined variable to the mechanism of clotting. As a result, the end point recorded may vary significantly from the true end point.

The instrument described in U.S. Pat. No. 3,836,333, in common with similar other instruments, depends on mechanical impedance, and therefore is subject to test to test variability due to the effect of a foreign body. This effect is enhanced when a relatively large volume of plasma or whole blood is employed, for example, in excess of 50 microliters, and is demonstrated in procedures such as dialysis, cardiac bypass and open heart surgery which require the extra corporeal circulation of the blood. The contact with foreign materials inherent in these procedures requires the administration of heparin to prevent clotting of the blood which would otherwise occur. It must therefore be assumed that the clotting time measured by mechanical impedance instruments is shortened by an undetermined increment, for the same reason. Unlike the effect of exposure to a glass surface of fixed dimensions, which is constant, that of the intrusive elements in motion relative to the blood may be variable within limits that have not been determined. Variability is further increased by the use of activators such as diatomaceous earth or glass particles to shorten coagulation time. Such activators, by nature of their particle size variability contribute to further uncertainties in the measurement of true clotting time. The following U.S. Pat. Nos. 3,635,678; 3,695,842; 3,967,934; 4,081,242; 4,125,327; 4,388,823; 4,599,219 all fall within the category of deficiencies defined for U.S. Pat. No. 3,836,333.

Despite the universal need for portability in clotting time instruments, and the growing constraints on medical costs, the instruments described in the foregoing patents are of limited utility in medical practice due to their relatively large size, complexity and cost, in addition to their operating deficiencies. The same conclusion follows, a fortiori in respect to U.S. Pat. 4,014,650. Clot detection based on ultrasonic generation is prohibitively expensive, due to the relatively complex equipment used. U.S. Pat. Nos. 3,699,437 and 3,841,643 teach a method of detecting clot formation and determining clotting time by an analog recording of changes in electrical resistance. The reliability of this method is based on the implicit, but questionable assumption, that the point of minimum resistance coincides with clot formation. Blood is an aequeous medium containing electrolytes including calcium, sodium, potassium and phosphorus, among others. The concentration of these ions will vary depending on the medical condition of the patient. Calcium deficiency is a known characteristic in such conditions as rickets and tetany. In other disorders, sodium may be present in undesirably high concentration. Electrical resistance of an aequeous medium varies in proportion to the concentration of electrolytes. The passage of current through such a medium will also affect its composition. For all of these reasons the reliability of resistance instruments, in the absence of positive and simultaneous confirmation (such as that provided by the slide method as described hereinafter in experiment II) must be questioned.

U.S. Pat. No. 4,217,107 teaches an indirect method of detecting clot formation, VIZ. by differentiation of the changes in the amount of scattered light measured discontinuously. The moment of clot formation is derived by mathematical inference, based on the assumption that first clot formation coincides with the first indication that the slope of the curve so generated has changed from positive to negative. As in the above listed patents the inferred time of clot formation has not been established by positive and simultaneous confirmation as in experiment II.

A similar system using light scatter techniques is shown in U.S. Pat. No. 4,252,536 wherein the resulting analog signal is digitized.

The instrument described in U.S. Pat. No. 4,756,884 is designed to measure and record APTT (Activated Partial Thromboplastin Time). The device is deficient in two respects. Its results have been shown to correlate poorly with standard laboratory procedures and APTT itself is a widely discredited test.

A generally recognized deficiency of the APTT method is reported in a paper entitled "Laboratory Monitoring of Heparin"—American Journal of Clinical Pathologists; October 1981. "A large change in APTT may correspond to only a small change in the Heparin concentration and thus may not be an indication for altering the Heparin dose." Otherwise stated, the relationship of the values reported, to the doses administered, is exponential when it should be linear for reliable and safe control. A test used by 85% of physicians, ("Thrombosis News" January 1983) is therefore known to be unreliable.

SUMMARY OF THE INVENTION

The present invention is a method and apparatus for the detection of blood coagulation by the use of infrared electromagnetic transmission changes through a sample caused by changes in blood composition as the blood clots. The present invention employs no intrusive element and provides a true accurate and reproducible detection of first clot formation and a like measurement of a like time elapsed from blood extraction to such first clot formation at peak I.R. response time. The progressive changes which occur after clot formation, culminating in a steady state response when the clot dries and completely solidifies, are also recorded in both digital and analog form and may provide useful information not heretofore available. The foregoing changes are recorded in digital and analog form by means of infrared electromagnetic transmission through a sample of whole blood extracted from a fingertip and deposited preferably in a circular glass slide receptacle. The slide is placed on a test stand opposite a source of infrared light such as an infrared emitting diode. A photodetector is placed in the optical path on the opposite side of the sample and changes in the blood composition are suitably measured and recorded.

DESCRIPTION OF THE DRAWINGS

FIGS. 7 through 10 are graphs showing blood coagulation plotted against time for experiments conducted using the apparatus of the present invention.

DESCRIPTION OF THE PREFERRED EMBODIMENTS

Figure 1:
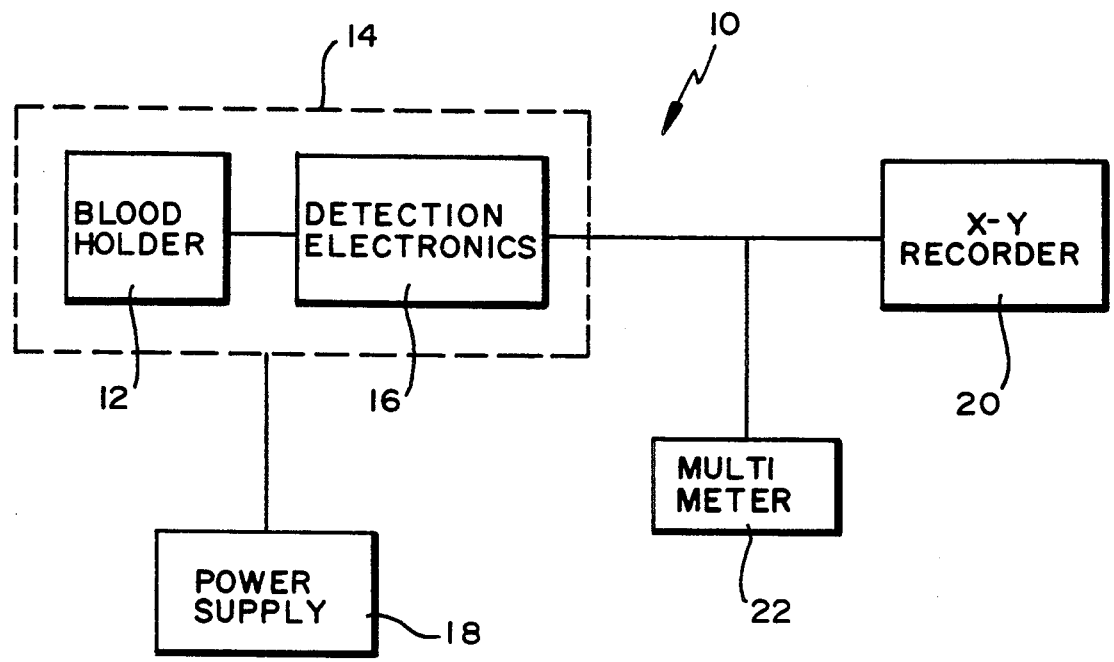
FIG. 1 is a block diagram of the infrared blood coagulation testing instrument of the present invention.

FIG. 1 illustrates a block diagram of a blood test apparatus 10 of the present invention. A blood holder 12 is placed in a suitable light shielded housing 14. Detection electronics 16 powered by a source of supply 18 is optically juxtaposed with the IR source of electromagnetic energy as described hereinbelow. The output of the detector electronics is fed to a suitable X-Y recorder 20 and to a suitable monitoring digital multimeter 22.

Figure 2:
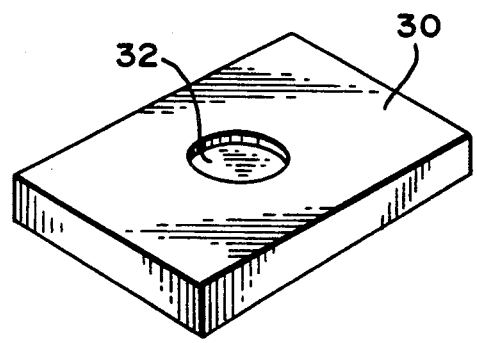
FIG. 2 is a perspective view of a blood sample holder used with the apparatus of FIG. 1.

Referring to FIG. 2, the blood sample holder is a suitable slide 30 having a centrally located circular receptacle having a predetermined volume capacity and sized preferably less than ½ inch in diameter and less than 1/16 inch in depth.

Figure 3:
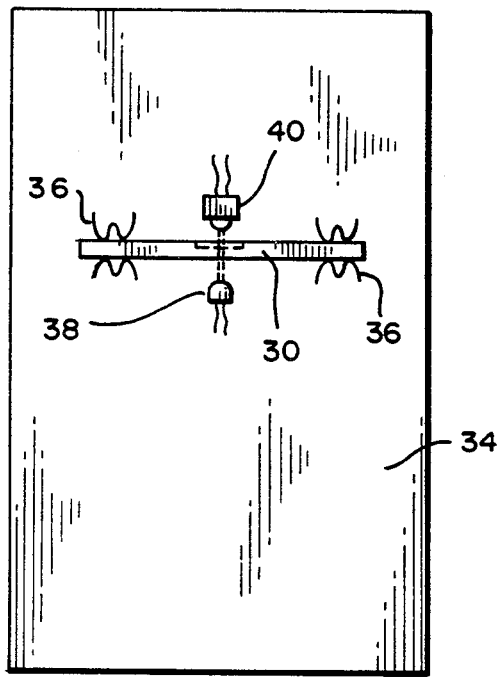
FIG. 3 is a diagrammatic view of the sample holder mounted with respect to the infrared optical path of the instrument.

FIG. 3 illustrates a printed circuit board 34 including a slide 30 mounted on suitable slide holder posts 36. An infrared light emitting diode 38 provides a source of electromagnetic light energy which passes through the blood sample held in the glass slide receptacle 32 to a corresponding photodetector 40 placed in the optical path of the electromagnetic energy.

Figure 4:
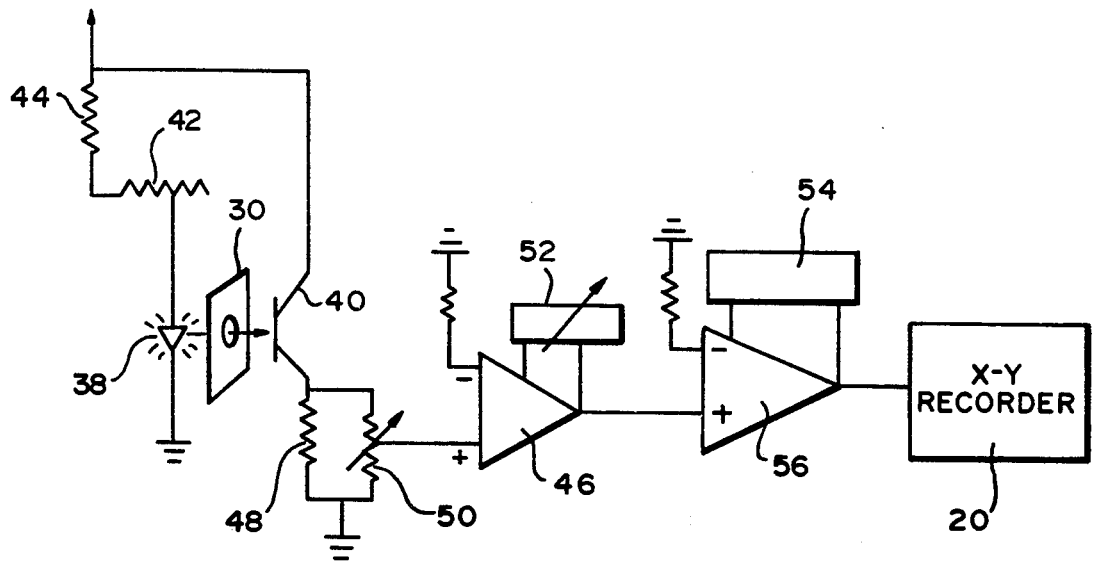
FIG. 4 is a circuit diagram of the detector electronics of the present invention.

Referring to the detector electronics shown in FIG. 4, the infrared light emitting diode 38 is connected to a 5 volt source of supply through variable resistor 42 and current limiting resistor 44. Photodector 40 is preferably an infrared light sensitive photo diode connected to a 5 volt source of supply and having its output connected to one input of an operational amplifier 46 by way of parallel of resistor circuit 48 and variable light level signal adjusting resistor 50.

Operational amplifier 46 is connected in the non-inverting mode and gain circuitry 52 is used to adjust the operational amplifier's output magnitude. The output of amplifier 46 is connected to the input of operational amplifier 56 which is connected in the inverting mode. The DC level of amplifier output 56 is adjusted by circuitry 54 in order to keep the pen of the X-Y recorder 20 on scale.

The infrared light emitter 38 and photodetector 40 pair is mounted vertically on the PC board 34 which includes the electronics shown in FIG. 4. The whole system except the recorder 20 and the multimeter 22 is enclosed in the light insulated housing 14, diagrammatically shown in FIG. 1.

Figure 5:
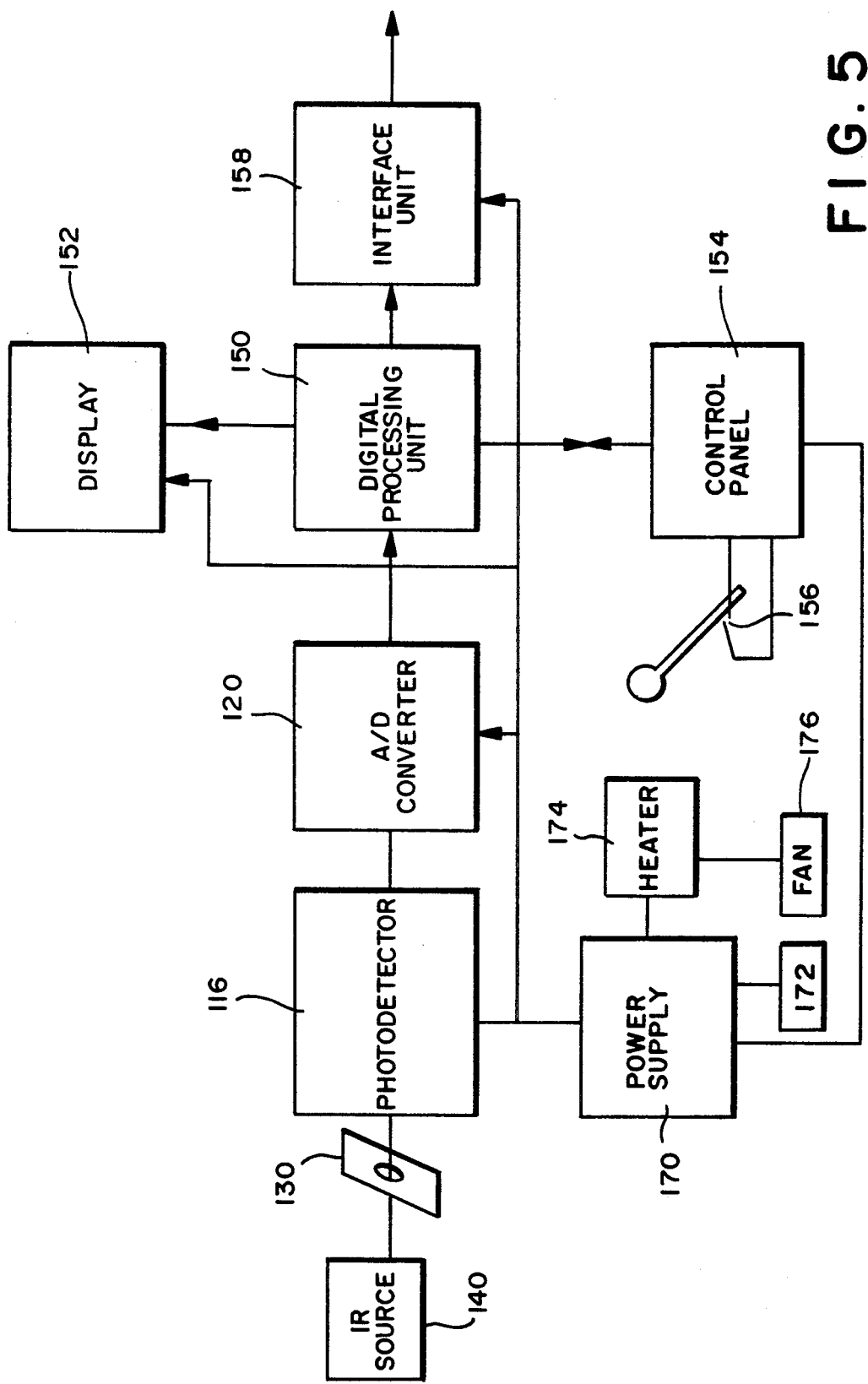
FIG. 5 is a view of a block diagram of a preferred embodiment of the invention.

Referring to FIG. 5, a more detailed block diagram of the proposed system is shown which provides a quick, accurate blood coagulation time in a hospital or other medical environment, such as the bedside of a patient or in operating rooms. In this preferred embodiment, a system output would be connected to an LED digital display read-out and/or a graphic printer (not shown). An infrared source 140 of the type described hereinabove emits a light beam through a sample held in a suitable slide 130 where it is received by photodetector circuit 116 and adjusted as described hereinabove. The output of the circuit 116 is connected to an A/D converter 120 which samples the analog output from the electronics and converts to a digital signal which is then sent to a digital processing unit 150. This unit 150 takes the digital signals and applies real time peak detecting algorithims to determine the exact peak of the coagulation curve as shown hereinabove. The digital process will then send the peak time to an LED display 152. The main purpose of this display 152 will be to indicate clotting time, "clot/no clot" indication and device status including "Ready", "in process," or "FAULT" indications. The digital processor 150 will also receive signals from the control panel 154 and the blood sample syringe sensing switch 156 described in detail hereinbelow. The control panel 154 provides suitable controls for turning power on/off, self test of unit, master reset and power supply switching. The digital processor 150 will also send data to an interface unit 158 which is connected to suitable data processing equipment, such as a standard serial interface to a PC type computer. Preferably, software will be supplied for the computer on a floppy disk that will allow the digital data that is sent from the digital processor to be labeled, categorized and printed out as a graph using a standard dot matrix printer, thus providing an analog counterpart to the basic digital information stored in memory.

The power supply 170 will power the entire unit with DC voltage from 110 ac input. Battery supply 172 will also power the unit through the output panel 154 when supply 170 is disabled.

A heater 174 is thermostatically controlled and set at 37 degrees C, normal blood temperature. A fan 176 circulates the air throughout the interior of the unit to simulate normal blood coagulation conditions.

Figure 6:
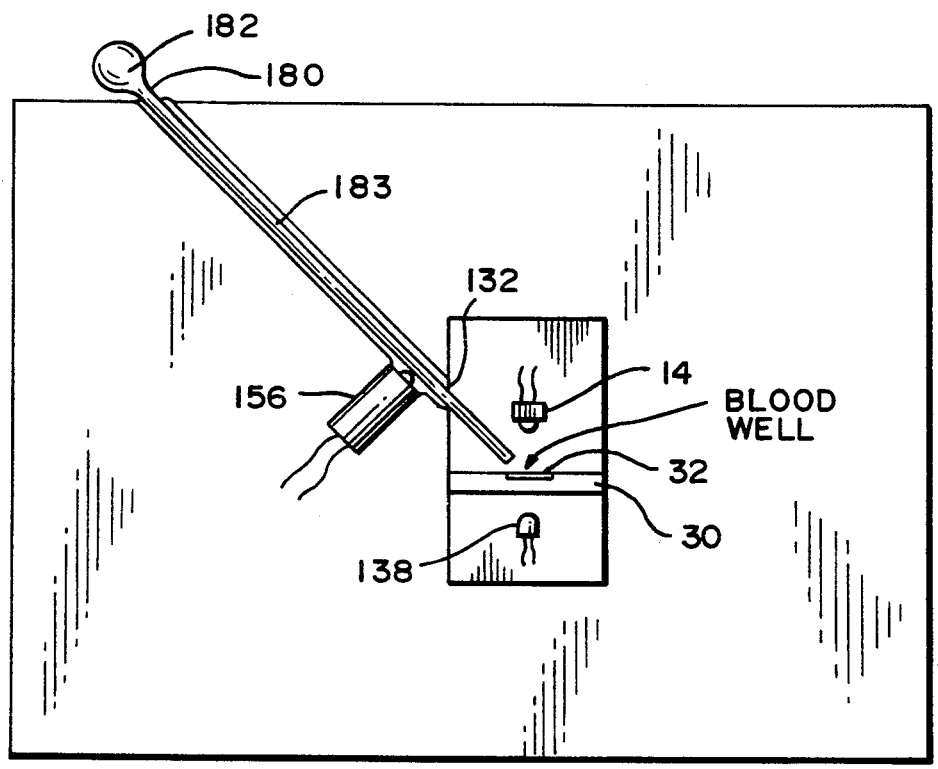
FIG. 6 is a diagrammatic view of a detail of the apparatus showing a sample being deposited onto the sample holder.

Referring to FIG. 6, a diagrammatic view of a detail of the invention is shown. A printed circuit board 134 includes an infrared light emitting diode 138, a sample slide 130 and a photodetector 140. The output of the photodetector 140 is fed through the analog circuitry on the printed circuit panel 130 to the digital processor 150. A syringe 180 contains the amount of blood to be sampled and is deposited in the slide well 32 using a bulb pump 182. The syringe 180 is placed into the end of a cylindrical guide tube 183 on top of the unit. A stop on the unit allows the end of the syringe 180 to be placed close enough to the slide 30 so that when the bulb 182 is squeezed, all the blood goes into the well 32 in the slide 30, and does not hang up in the tube or interfere with the I.R. path. When the syringe 180 is inserted into the machine, the microswitch 156 connected to the control panel 154 is tripped and the microprocessor 150 is armed to get ready to take data. The software timer is started which allows 5 seconds before the data begins to be processed to enable time to squeeze the blood out onto the slide holder. The syringe 180 is made of plastic material which is essential in delaying the blood clotting process until the blood can be deposited into the glass slide well 32, because whole blood in contact with a plastic surface will not coagulate, whereas a glass surface acts as a catalyst to the coagulation process. Both the syringe 180 and the cylindrical guide tube 183 are disposable in order that sterile and uncontaminated ones are available for each clotting time measurement.

Using the apparatus of the present invention for measuring the clotting characteristics of blood, the following experiments were conducted.

Experiment I

The first step is extracting the blood. After the finger is lanced, the blood is drawn into a capillary tube pipet that holds exactly 50 microliters (the slide well capacity). Next, the blood is emptied into the slide well mounted in the housing holder and centered under the infrared emitting diode. The top is then replaced on the housing and the D.C. offset is adjusted to place the pen midway on the Y axis. The pen is adjusted to the start of the time axis and is swept at sec/inch. Loading recorder ink pens, setting the time axis and loading the paper are all standard operations.

FIG. 7 shows two clotting curves of typical results. The bottom curve 70 is plotted against increments of 25 seconds per square, whereas the top curve 72 is the same curve compressed and plotted against increments of 125 seconds per square, and demonstrates the overall curve shape better. Both curves for "regular blood" peak at about 225 seconds.

Experiment II

Figure 8:
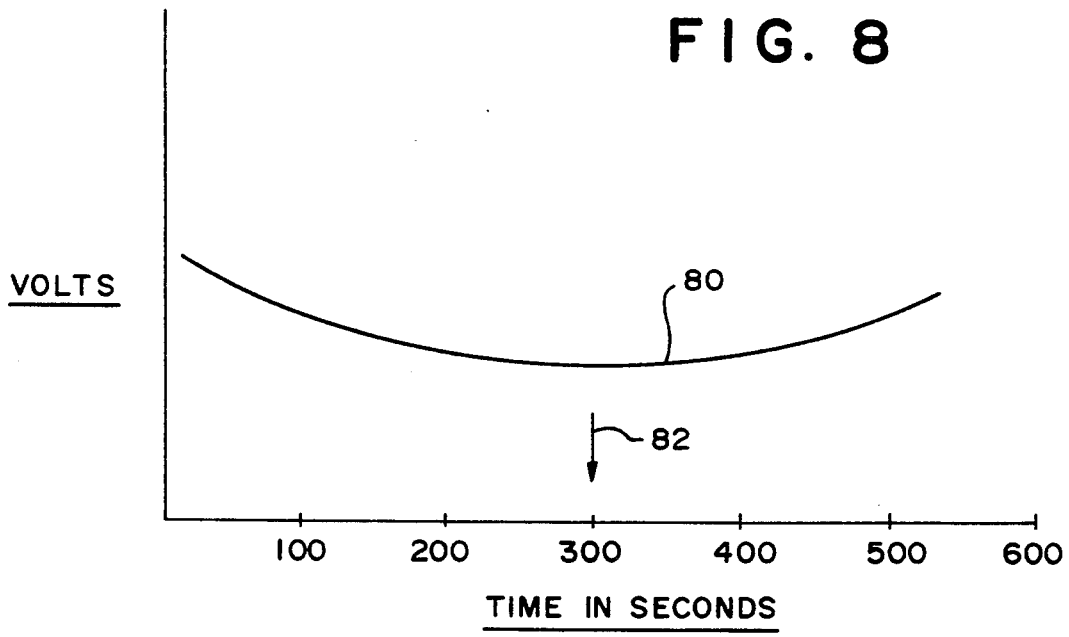

In order to further substantiate the claim that the peak of the infrared curve closely corresponds with blood coagulation, another standard slide method experiment was run using the same donor. In this experiment, a double blood sample was taken from the donor; half of the sample was used in a slide in the infrared instrument of the present invention and half in a slide that the technician tested every 15 seconds by dipping a pin into the blood filled well until clots were visible on the pin using a well known slide method as described in the Manual of Clinical Laboratory Methods by Opal E. Hepler, M.D. (Fourth Edition, Ninth Printing.) Three runs all produced differences of less than 15 seconds between the time of blood coagulation detected on the pin and the peak of the curve from the infrared device. Referring to FIG. 8, the clotting curve 80 shows the results of the clotting time using the invention apparatus which records peak voltage representing clotting in terms of infrared light transmission levels verses time, whereas the arrow 82 represents the time when the technician detected a clot manually. As can be seen from the figure, the peak of the plotted curve generally corresponds to the time the clot was detected manually.

Experiment III

Figure 9:
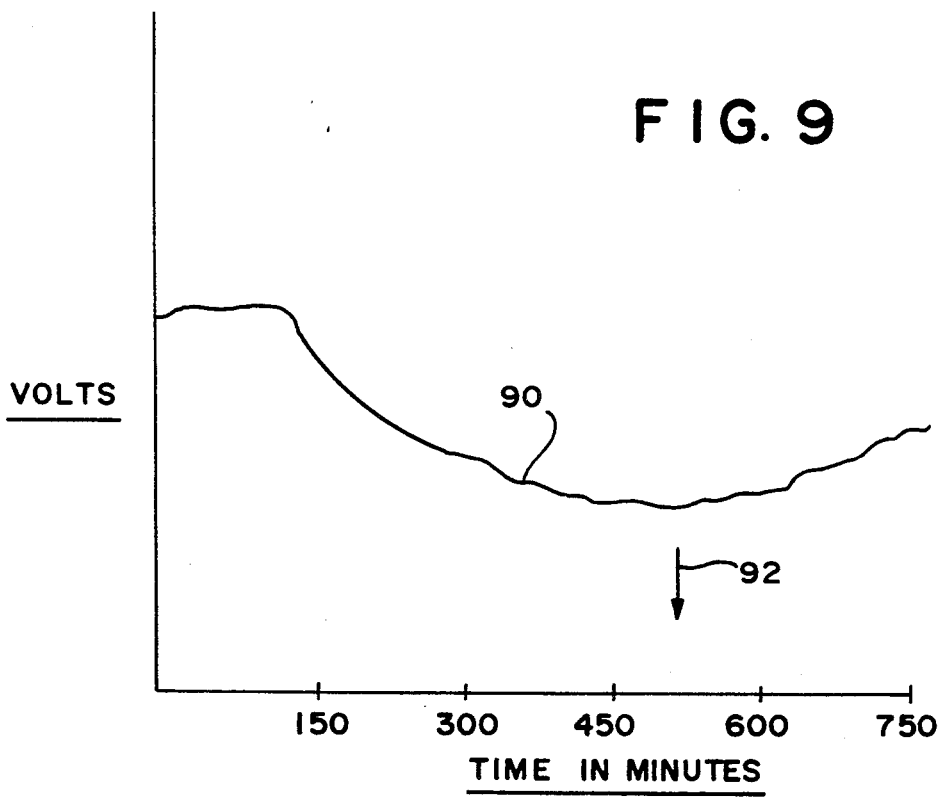

A further experiment involved adding Heparin to blood samples, observing the curve peaking times and checking them against the Slide Method. Referring to FIG. 9, the infrared instrument recorded coagulation at the maximum point of the X axis of the curve 90. The times were within 25 seconds of the Slide Method results, the arrow 92 representing the time a clot was detected manually.

Experiment IV

Figure 10:
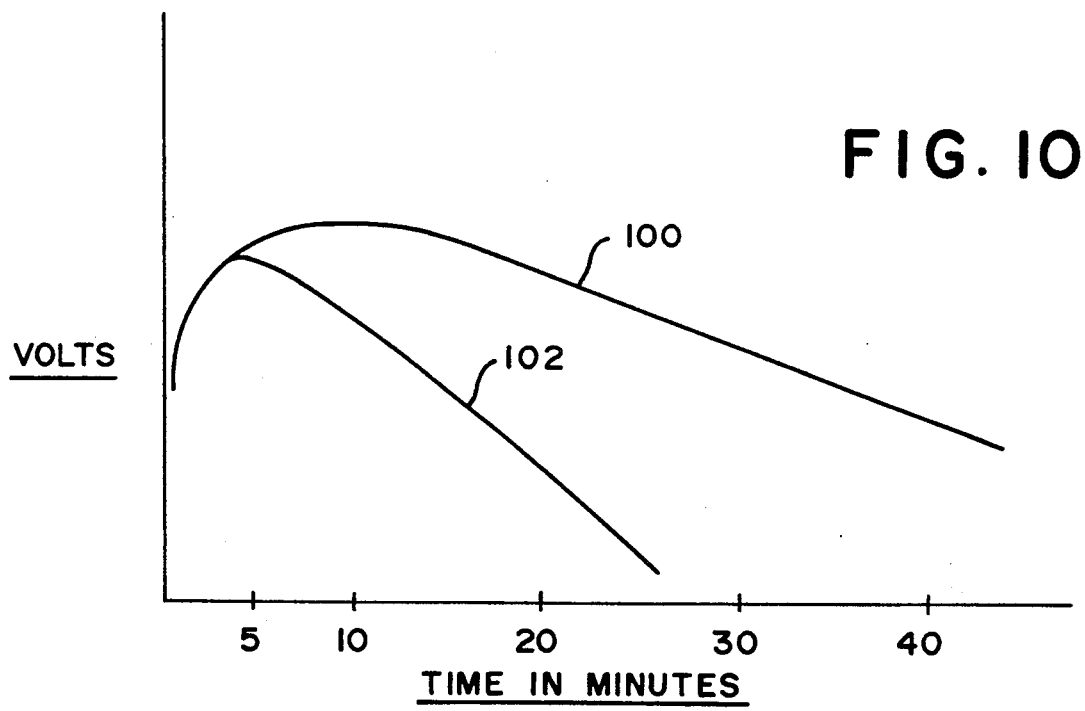

A further experiment, used blood from the same donor and checked the clotting time with and without the addition of Heparin to the same sample. Referring to FIG. 10, the plotted results show the clotting time increases in the Heparin blood sample as shown in the plotted curve 100 as compared to whole blood without Heparin as shown in the plotted curve 102.

I claim:

1. A method recording the clotting time of whole blood as it proceeds from fibrinogen through known stages of coagulation, culminating in the cross-linking of the fibrin clot which ultimately solidifies and dries at the end of a cycle, including the steps of:

providing a measured sample of whole blood to be tested;

transmitting infrared electromagnetic energy through the blood sample;

detecting the transmission of the infrared energy and electronically producing the signals in response to said infrared energy; and measuring a peak transmission level of said infrared energy and calibrating said peak signal in terms of clotting time of said whole blood sample whereby the clotting time is represented by the peak transmission level of the infrared energy through the whole blood sample.

2. The method of claim 1 wherein the step of providing a sample includes drawing blood from the fingertip of a subject and depositing the sample in a receptacle using a delivery capillary tube fitted with a rubber bulb which delivers the sample to the receptacle when it is squeezed by the instrument operator.

3. The method of claim 2 further including the step of inhibiting the clotting process by use of a plastic capillary delivery tube until the sample is deposited within said receptacle.

4. The method of claim 1 wherein the sample deposited in the receptacle is whole blood.

5. An instrument for measuring and recording the clotting time of blood by measuring changes in the amplitude of an electromagetic energy transmission through the blood coinciding with changes in the composition of the blood as it proceeds from fibrinogen through known stages of coagulation culminating in the cross-linking of the fibrin clot which ultimately solidifies and dries at the end of a cycle represented by a peak amplitude of the electromagnetic energy transmission comprising:
- a measured sample to be tested;
- means for transmitting a source of infrared electromagnetic energy through said sample;
- detector means for measuring changes in amplitude of said infrared electromagnetic energy signal;
- circuit means for providing a signal representative of said changes in amplitude; and,
- means for producing a signal calibrated in terms of coagulation time when peak infrared transmission is recorded.

6. The instrument of claim 5 wherein said transmitting means is an infrared light emitting diode.

7. The instrument of claim 5 further including means to record said signal to provide a permanent record thereof.

8. The instrument of claim 7 further including power supply means for providing power to said instrument.

9. The instrument of claim 5 further including analog circuitry for detecting said changes in amplitude, analog to digital convertor for providing a digital output representative of said amplitude changes, digital processor means for providing an output signal display means and recording means connected to said digital processor to display and record said signals in terms of coagulation time.

10. The instrument of claim 5 further including control panel means and switch means actuated in response to the insertion of a blood sample in a sample holding means; whereby actuation of said switch means begins a test cycle.

11. An instrument for measuring and recording clotting time of blood by measuring changes in amplitude of an infrared energy transmission through a blood sample coinciding with changes in the composition of the blood as it proceeds from fibrinogen through known stages of coagulation culminating in the cross-linking of a fibrin clot which ultimately solidifies and dries at the end of the cycle represented by a peak amplitude of the infrared energy transmission, comprising:
- means for holding a measured sample to be tested;
- means for transmitting a source of infrared electromagnetic energy through the sample;
- detector means for measuring changes in amplitude of said infrared electromagnetic energy signal;
- circuit means for providing a signal representative of said changes in amplitude;
- means for producing a signal calibrated in terms of coagulation time when peak infrared transmission is recorded; and
- a cylindrical channel extending from the exterior of the instrument to a point adjacent said sample holding means, said channel constructed to receive a cylindrical capillary delivery tube to precisely deposit and locate said sample to be tested on said sample holding means.

12. The instrument of claim 11 further including switching means adjacent said cylindrical channel and operable in response to said capillary delivery tube, said switch means being connected to a suitable control means for beginning the operation of a test cycle.

13. The instrument of claim 11 in which the blood sample holding means and said cylindrical capillary delivery tube are both disposable.

* * * * *

US005167145B1

REEXAMINATION CERTIFICATE (4086th)

United States Patent [19]
Butler et al.

[11] B1 5,167,145
[45] Certificate Issued May 23, 2000

[54] MEASUREMENT OF BLOOD COAGULATION TIME USING INFRARED ELECTROMAGNETIC ENERGY

[75] Inventors: David M. Butler, 529 Chesapeake Ave., Stevensville, Md. 21666; Harold B. Kirkpatrick, 830 W. 40th St., Baltimore, Md. 21217; John H. Staehlin, Mays Chapel Rd., Lutherville, Md. 21093

[73] Assignees: David M. Butler, Stevensville; Harold B. Kirkpatrick, Baltimore; John H. Staehlin, Lutherville, all of Md.

Reexamination Request:
No. 90/005,208, Dec. 31, 1998

Reexamination Certificate for:
Patent No.: 5,167,145
Issued: Dec. 1, 1992
Appl. No.: 07/584,789
Filed: Sep. 19, 1990

[51] Int. Cl.[7] .......................... G01N 21/17; G01N 33/49
[52] U.S. Cl. .......................... 73/64.43; 73/64.41; 356/39; 422/73; 436/69; 250/341.5; 250/343

[58] Field of Search .......................... 73/64.43, 64.41; 356/39; 436/69; 422/73; 250/564, 573, 576, 341.5, 343, 340

[56] References Cited

U.S. PATENT DOCUMENTS

| 3,834,241 | 9/1974 | Garren et al. . |
| 4,695,430 | 9/1987 | Coville et al. .......................... 422/65 |
| 5,073,347 | 12/1991 | Garren et al. .......................... 422/100 |
| 5,114,860 | 5/1992 | Hayashi .......................... 73/64.41 X |
| 5,156,241 | 10/1992 | Grossman et al. .......................... 436/89 |
| 5,298,224 | 3/1994 | Plum .......................... 73/64.43 X |

FOREIGN PATENT DOCUMENTS

| 120 715 | 10/1984 | European Pat. Off. . |
| 404 260 | 9/1978 | Sweden . |
| WO 89/06803 | 7/1989 | WIPO . |

*Primary Examiner*—Thomas P. Noland

[57] ABSTRACT

A method and apparatus for detection of blood coagulation using infrared electromagnetic transmission changes through a sample from a source of infrared energy to suitable detection electronics producing a peak signal representative of the clotting time.

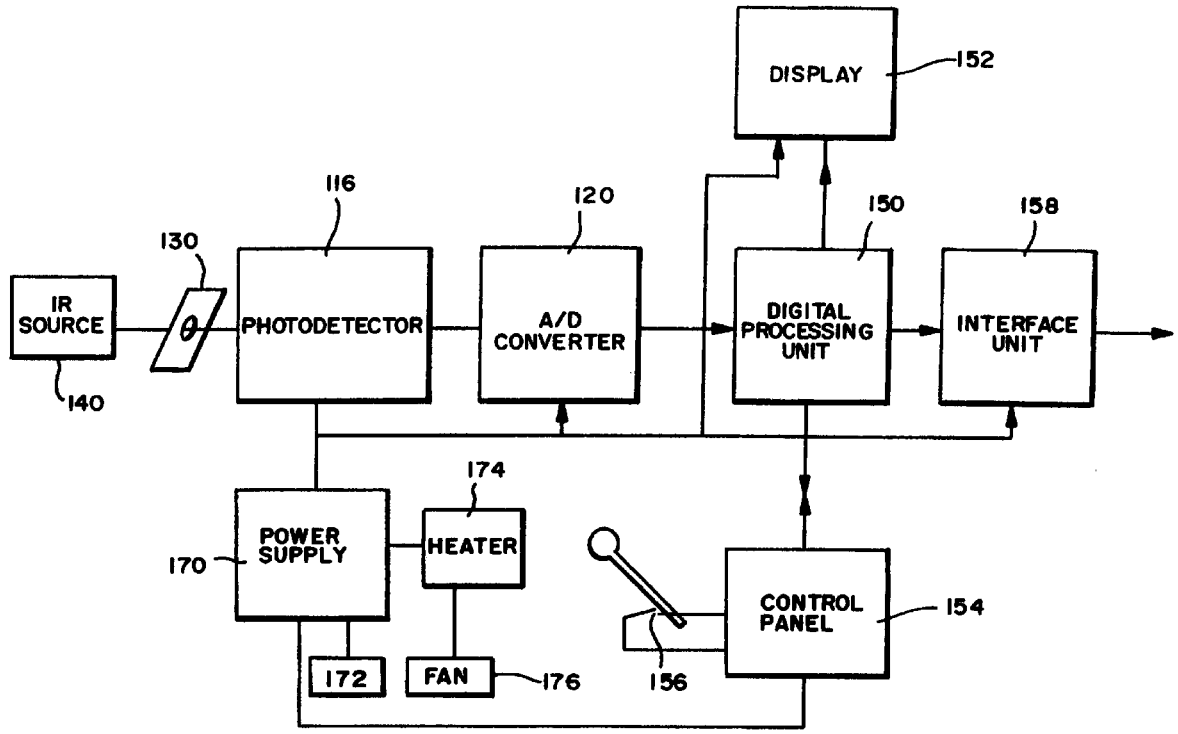

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–13 is confirmed.

* * * * *